(12) United States Patent
Akutsu et al.

(10) Patent No.: US 11,662,357 B2
(45) Date of Patent: May 30, 2023

(54) AUTOMATED ANALYSIS DEVICE

(71) Applicant: Hitachi High-Technologies Corporation, Tokyo (JP)

(72) Inventors: Masashi Akutsu, Tokyo (JP); Naoto Suzuki, Tokyo (JP); Hiroki Fujita, Tokyo (JP); Akihiro Yasui, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 16/646,410

(22) PCT Filed: Oct. 29, 2018

(86) PCT No.: PCT/JP2018/040044
§ 371 (c)(1),
(2) Date: Mar. 11, 2020

(87) PCT Pub. No.: WO2019/116751
PCT Pub. Date: Jun. 20, 2019

(65) Prior Publication Data
US 2020/0271678 A1   Aug. 27, 2020

(30) Foreign Application Priority Data
Dec. 15, 2017  (JP) .............................. JP2017-241191

(51) Int. Cl.
*G01N 35/02*  (2006.01)
*G01N 35/00*  (2006.01)
(Continued)

(52) U.S. Cl.
CPC ....... *G01N 35/02* (2013.01); *G01N 35/00603* (2013.01); *A61K 35/14* (2013.01);
(Continued)

(58) Field of Classification Search
CPC .. G01N 35/02; G01N 35/00603; G01N 35/04; G01N 27/447; G01N 35/00;
(Continued)

(56) References Cited

U.S. PATENT DOCUMENTS 4,965,049 A * 10/1990 Lillig ................... G01N 35/025
                                                   422/68.1
5,232,081 A    8/1993 Kanamori
(Continued)

FOREIGN PATENT DOCUMENTS

EP   1 248 113 A1   10/2002
JP   H1130618 A  *  2/1992 ............. G01N 35/02
(Continued)

OTHER PUBLICATIONS

International Search Report (PCT/ISA/210) issued in PCT Application No. PCT/JP2018/040044 dated Dec. 25, 2018 with English translation (five (5) pages).
(Continued)

*Primary Examiner* — Benjamin R Whatley
*Assistant Examiner* — Curtis A Thompson
(74) *Attorney, Agent, or Firm* — Crowell & Moring LLP

(57) ABSTRACT

This automated analysis device is provided with a plurality of analysis units for analyzing a specimen, a buffer portion which holds a plurality of specimen racks on which are placed specimen containers holding the specimen, a sampler portion which conveys the specimen racks held in the buffer portion to the analysis units, and a control portion which, when performing a process to deliver the specimen racks to the plurality of analysis units, outputs synchronization signals to all the plurality of analysis units, wherein the analysis unit performs a delivery process starting from the synchronization signal, and the analysis unit performs a delivery process starting from the synchronization signal.

10 Claims, 6 Drawing Sheets

(51) Int. Cl.
| | |
|---|---|
| *G01N 27/447* | (2006.01) |
| *A61P 7/00* | (2006.01) |
| *A61K 35/14* | (2015.01) |
| *A61M 1/02* | (2006.01) |
| *G01N 37/00* | (2006.01) |
| *G01N 35/04* | (2006.01) |

(52) U.S. Cl.
CPC ............... *A61M 1/02* (2013.01); *A61P 7/00* (2018.01); *G01N 27/447* (2013.01); *G01N 35/00* (2013.01); *G01N 35/04* (2013.01); *G01N 37/00* (2013.01); *G01N 2035/00752* (2013.01); *G01N 2035/00831* (2013.01)

(58) Field of Classification Search
CPC ......... G01N 37/00; G01N 2035/00752; G01N 2035/00831; G01N 2035/0415; G01N 2035/0439; G01N 2035/0462; G01N 2035/00326; A61P 7/00; A61K 35/14; A61M 1/02
See application file for complete search history.

(56) References Cited

U.S. PATENT DOCUMENTS

| | | | | |
|---|---|---|---|---|
| 7,842,237 | B1* | 11/2010 | Shibuya | G01N 35/026 422/64 |
| 2002/0169518 | A1* | 11/2002 | Luoma, II | G01N 35/0095 700/218 |
| 2004/0186360 | A1* | 9/2004 | Suzuki | G01N 35/026 600/310 |
| 2008/0056944 | A1* | 3/2008 | Nakamura | G01N 35/00712 422/67 |
| 2008/0310999 | A1 | 12/2008 | Yagi et al. | |
| 2009/0081794 | A1* | 3/2009 | Wakamiya | G01N 35/0092 436/43 |
| 2011/0054800 | A1* | 3/2011 | Mizumoto | G01N 35/00584 702/21 |
| 2011/0200485 | A1* | 8/2011 | Akutsu | G01N 35/00712 422/67 |
| 2012/0107793 | A1* | 5/2012 | Tatsutani | G01N 1/312 436/55 |
| 2012/0174687 | A1* | 7/2012 | Ohga | G01N 35/026 73/864.81 |
| 2012/0179405 | A1* | 7/2012 | Yano | G01N 35/02 702/85 |
| 2013/0117042 | A1* | 5/2013 | Tajima | G01N 35/0095 705/2 |
| 2014/0170023 | A1 | 6/2014 | Saito et al. | |
| 2015/0118756 | A1* | 4/2015 | Pollack | G01N 35/0095 436/43 |
| 2016/0033539 | A1* | 2/2016 | Zhang | G01N 35/00584 436/501 |
| 2018/0017588 | A1* | 1/2018 | Fujita | G01N 35/025 |

FOREIGN PATENT DOCUMENTS

| | | | | |
|---|---|---|---|---|
| JP | 7-167866 | A | | 7/1995 |
| JP | 10-19899 | A | | 1/1998 |
| JP | 2000088860 | A | * | 3/2000 ............ G01N 35/00 |
| JP | 2003-50241 | A | | 2/2003 |
| JP | 2007-309743 | A | | 11/2007 |
| JP | 2008-39554 | A | | 2/2008 |
| JP | 2008-281453 | A | | 11/2008 |
| JP | 2013117538 | A | * | 6/2013 ............ G01N 35/02 |
| JP | 2014062760 | A | * | 12/2014 ............ G01N 35/00 |
| WO | WO 01/51929 | A1 | | 7/2001 |

OTHER PUBLICATIONS

Japanese-language Written Opinion (PCT/ISA/237) issued in PCT Application No. PCT/JP2018/040044 dated Dec. 25, 2018 (five (5) pages).
Japanese-language International Preliminary Report on Patentability (PCT/IPEA/409) issued in PCT Application No. PCT/JP2018/040044 dated Dec. 10, 2019 (five (5) pages).
Notification of Transmittal and English Translation of International Preliminary Report on Patentability issued in PCT Application No. PCT/JP2018/040044 dated Jun. 18, 2020 (nine (9) pages).
Extended European Search Report issued in European Application No. 18888159.3 dated Sep. 7, 2021 (nine (9) pages).

\* cited by examiner

[FIG. 1]
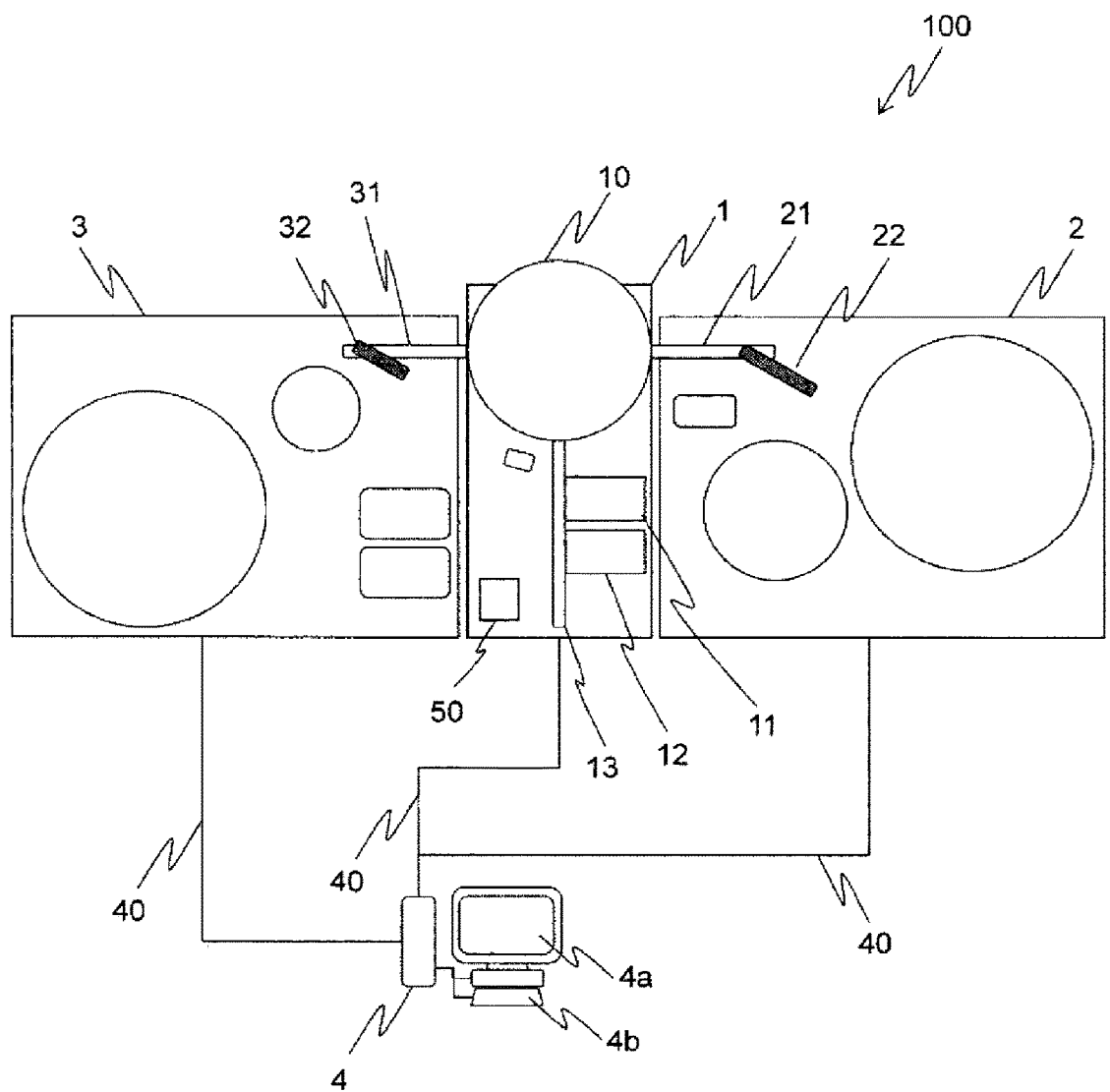

[FIG. 2]
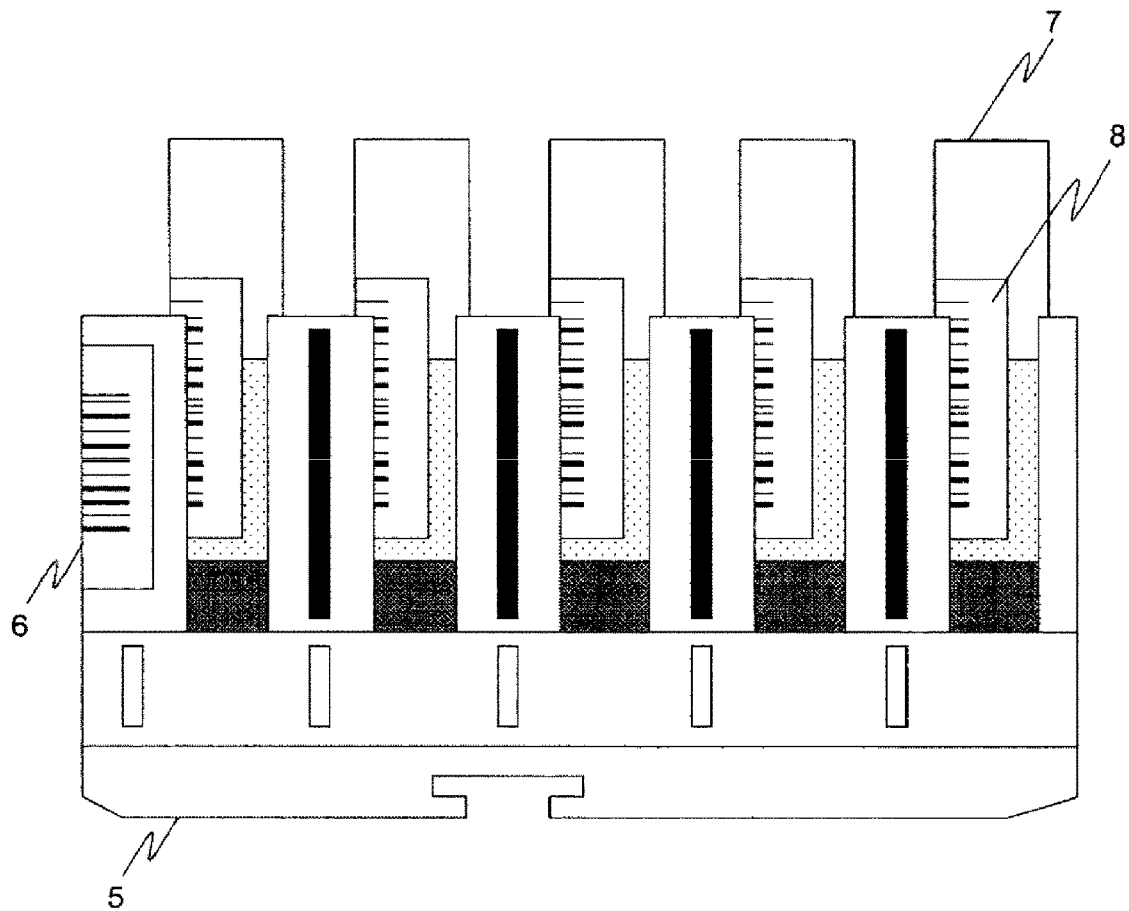
[FIG. 3]
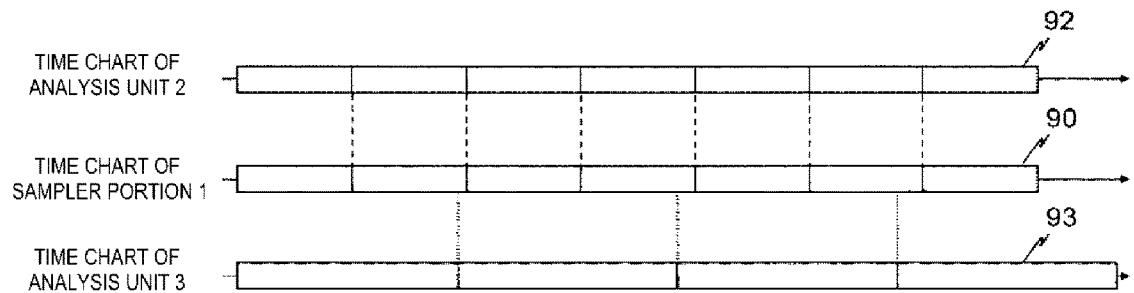

[FIG. 4]
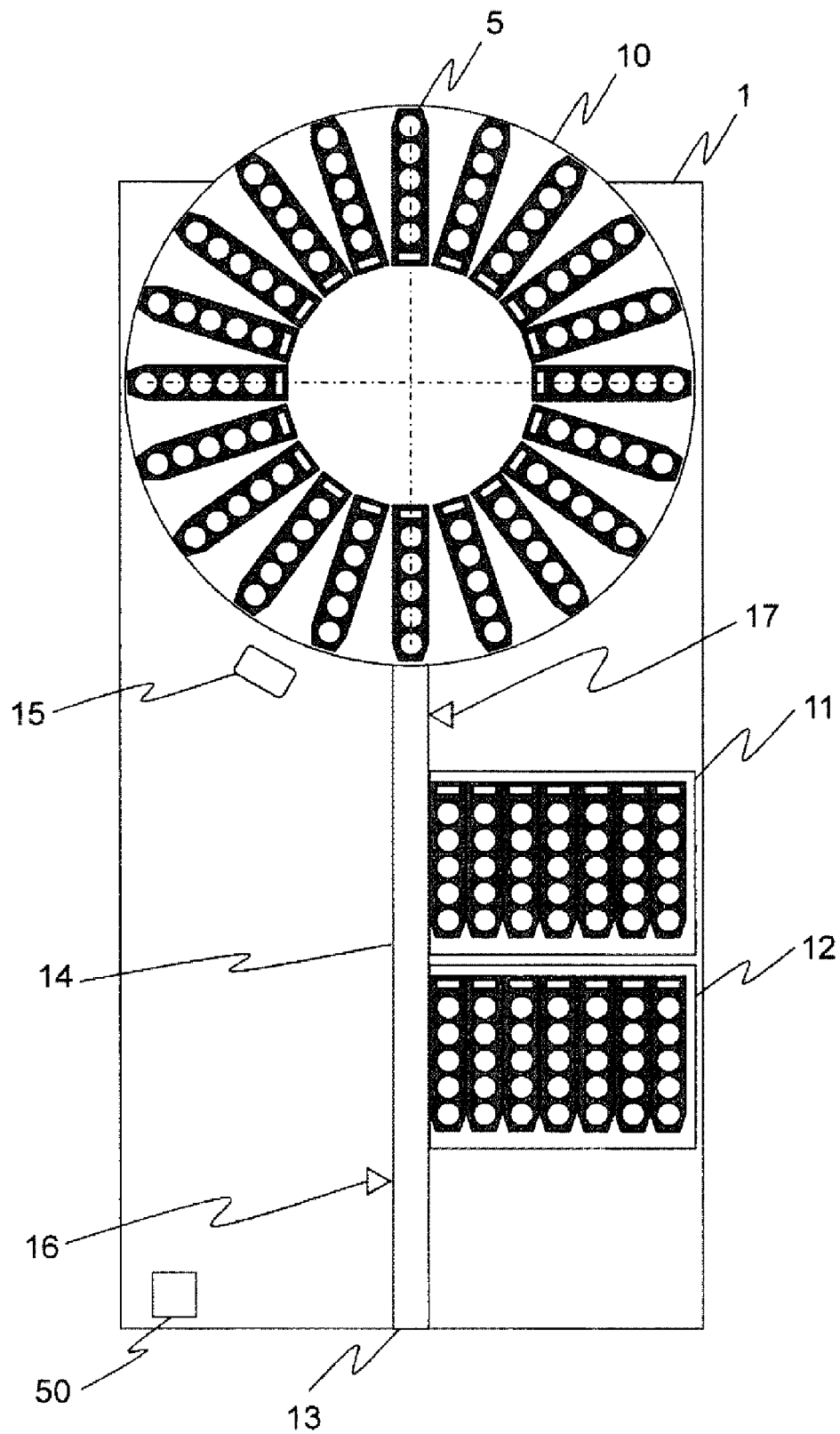

[FIG. 5]
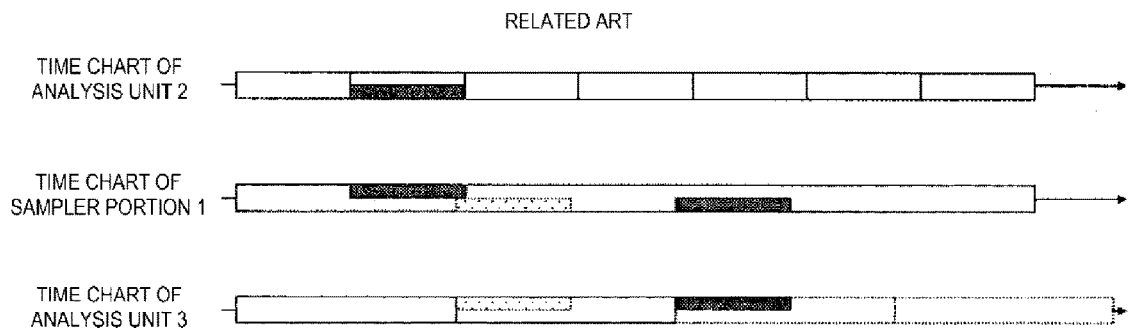
[FIG. 6]
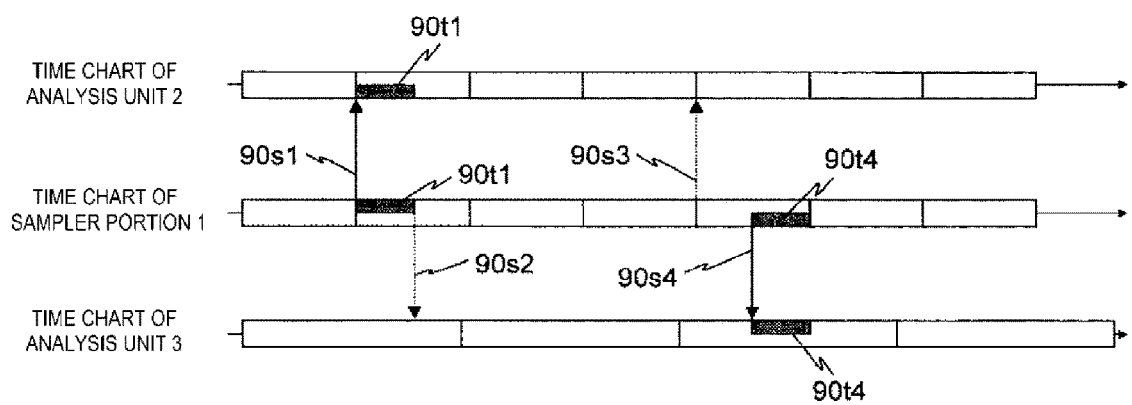
[FIG. 7]
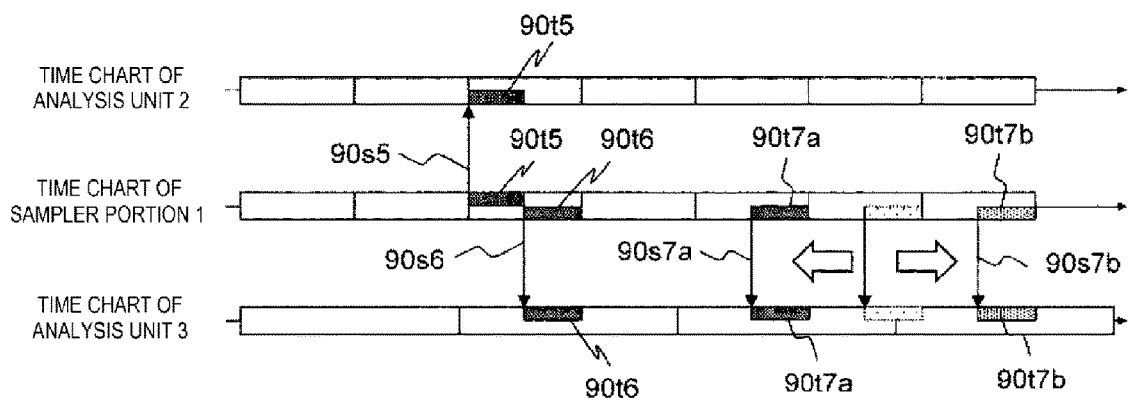

[FIG. 8]
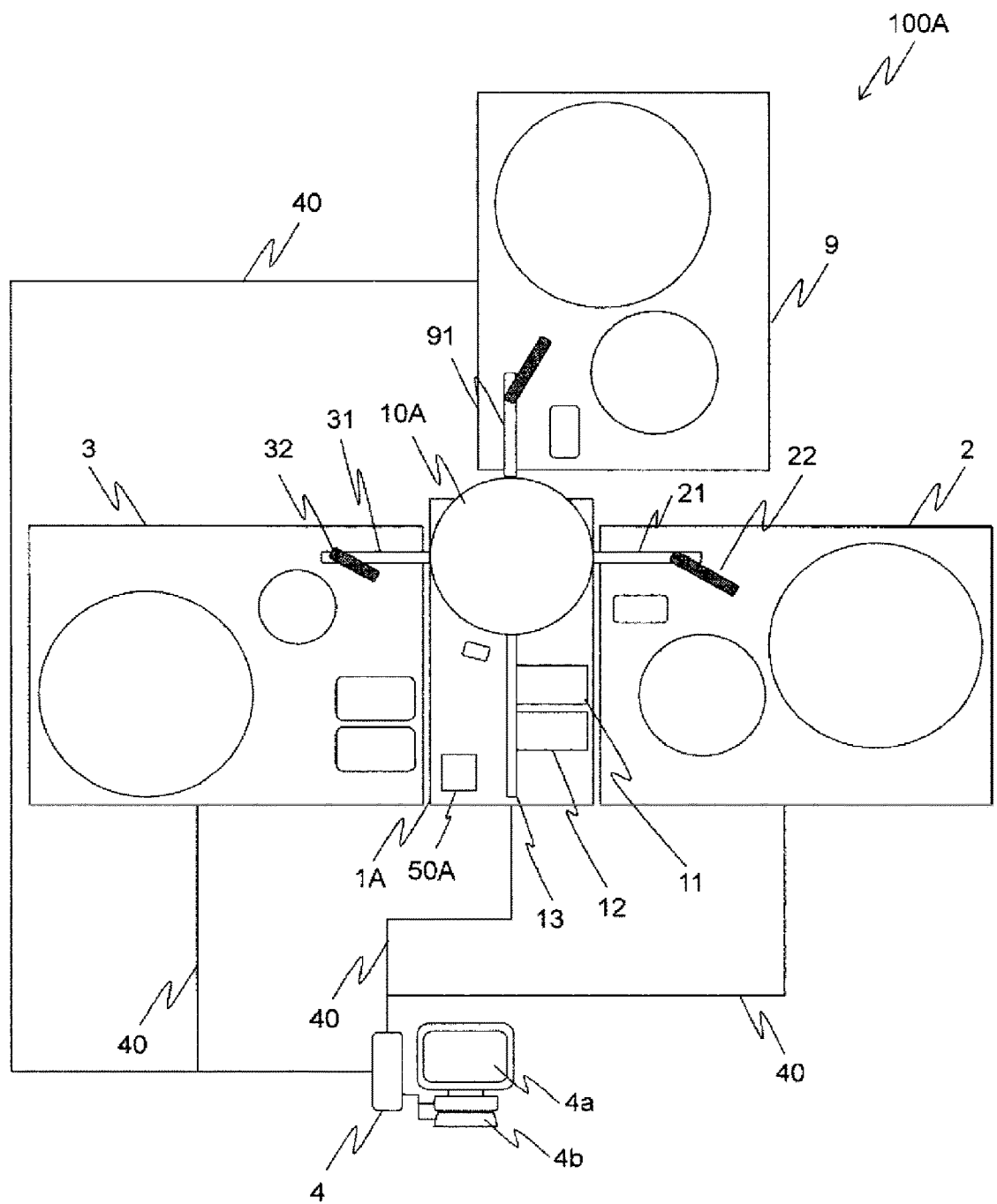

[FIG. 9]
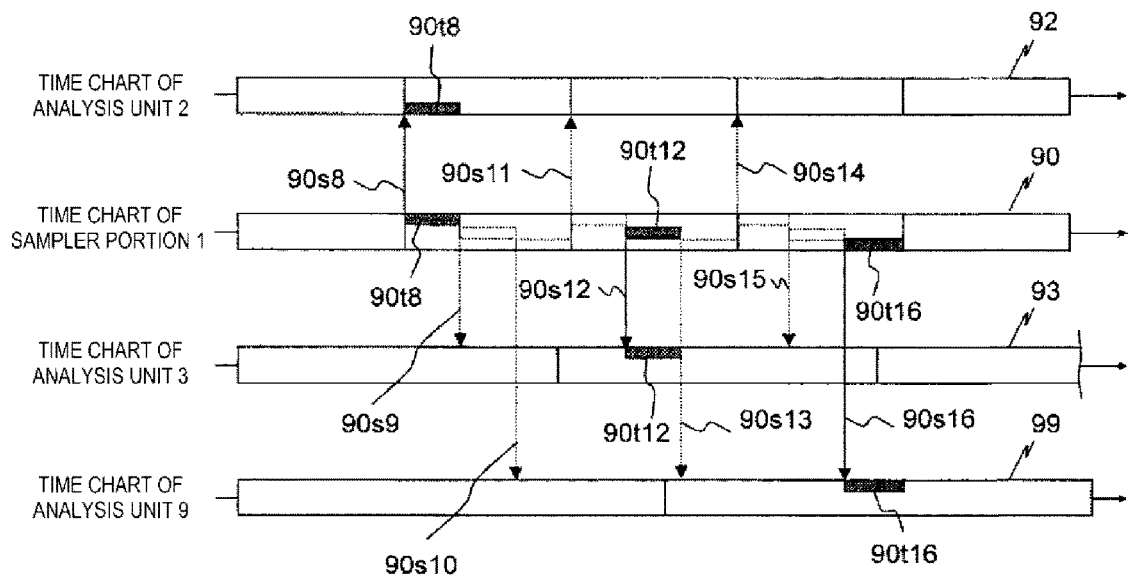
[FIG. 10]
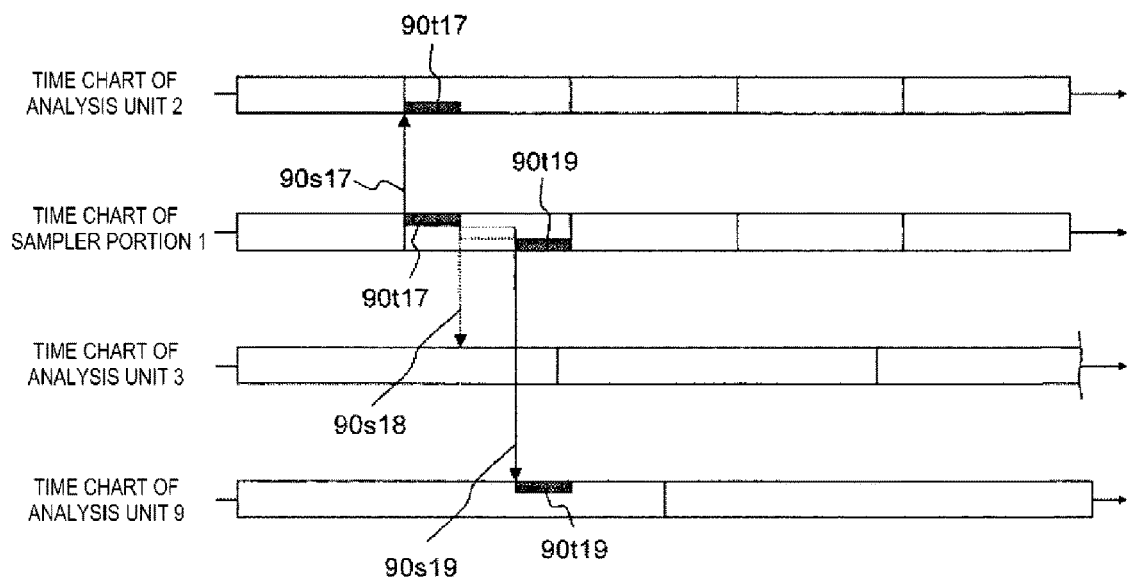

AUTOMATED ANALYSIS DEVICE

TECHNICAL FIELD

The present invention relates to an automated analysis device that quantitatively and qualitatively analyzes biological specimens (hereinafter referred to as specimens) such as blood and urine, and particularly relates to an automated analysis device including a conveyance device that conveys a specimen container to the analysis device.

BACKGROUND ART

Patent Literature 1 discloses an example of a simple and low-cost specimen conveyance device whose scale does not increase even when a belt line is bypassed or extended. Patent Literature 1 discloses a technique in which primary specimens are separately dispensed into different usage analysis devices, that is, a specimen rack C1 using an analyzer as a destination and a specimen rack C2 using a different analyzer as a destination, a rack merging device merges the specimen rack C1 and the specimen rack C2 on a main conveyance line, and a rack branching device allocates the specimen rack C1 and the specimen rack C2 that are conveyed on the main conveyance line to an analysis device conveyance line D1 or an analysis device conveyance line D2. The analysis device conveyance line D1 and the analysis device conveyance line D2 are provided respectively in the usage analysis devices.

PRIOR ART LITERATURE

Patent Literature

PTL 1: JP-A-7-167866

SUMMARY OF INVENTION

Technical Problem

An automated analysis device that automatically performs quantitative and qualitative analyses on specimens such as blood and urine is mainly and widely used in a university hospital and a clinical examination center where a large number of patient specimens need to be processed in a short time. Various automated analysis devices of a large size, a medium size, and a small size have been developed according to process capacities.

In particular, in a case of a large analysis device that analyzes a large number of specimens, specimen containers containing specimens are conveyed to a plurality of analysis units via conveyance lines (conveyance devices) in a state in which the specimen containers are held in holders which are referred to as specimen racks, so that the analysis device automatically performs analyses until an output of the analysis device with a laboratory technician simply placing the racks into a specimen rack intake.

In recent years, connected analysis units are used for many applications. Examples include a biochemical analysis device that measures blood cholesterol and the like, an immune analysis device that measures infectious diseases and the like, and an analysis device in which a plurality of different analysis units are connected.

This accordingly leads to a flow in which not only a large number of specimens are measured, but also various types of items are measured. Since the automated analysis device can be integrated, a connection form by a conveyance line, which was mainly used in a large size in the related art, can also be used in medium and small automated analysis devices and widely used in a medium hospital or the like.

In general, an analysis device performs in parallel a plurality of analysis steps in a pipeline process manner so as to improve a process capacity. That is, a constant analysis cycle is repeatedly performed.

Therefore, a mechanism is controlled by a time chart method in which the same operations are repeated at a predetermined time.

However, since the biochemical analysis device and the immune analysis device as described above have different analysis steps, analyses are performed by controlling the mechanism based on a time chart defined by analysis cycles that are different from each other, and analysis processes are performed in parallel to each other in different time cycles.

When analysis units having different analysis cycles are connected and operated as an integrated system, a difference of the analysis cycles needs to be absorbed.

Here, a conveyance line is connected to the analysis units. When one analysis unit is preferentially operated, operation of another analysis unit would be hindered. That is, control needs to be performed to not hinder the operation of the other analysis unit while maintaining certain synchronization between the analysis unit and the conveyance line.

As a solution, it is common practice to provide a dedicated conveyance line for an analysis unit and use the dedicated conveyance line as a buffer for interference between process capacities. However, providing such a dedicated conveyance line requires a complicated mechanism, which may increase production costs and a difficulty of adjusting the mechanism, and may reduce a measurement speed of patient specimens that require an urgent measurement.

A mechanism that prevents a process capacity from being lowered by controlling a buffered number is also studied. However, in normal operation of a hospital, the number of specimens that arrives during day time varies in a large number of specimen processes of specimen measurements for in-hospital patients in the morning, specimen measurements for outpatients from around noon, and specimen measurements for sparsely arrived emergency patients after evening. Since emergency degrees, examination items, and the like required at each time are different, control by a simple setting is not applicable in actual operation.

Therefore, although it would be good if a specimen can be conveyed to another analysis unit when one analysis unit is busy, this cannot be easily achieved. This is because the analysis unit that was busy may be no longer busy when the specimen is conveyed to the other analysis unit that was not busy.

An object of the invention is to provide an automated analysis device capable of conveying specimen containers to a plurality of analysis units without separately providing dedicated conveyance lines or affecting operation of the analysis units.

Solution to Problem

Although the invention includes a plurality of solutions to the problems described above, one example of the solutions is described. An automated analysis device that analyzes specimens includes a plurality of analysis units that analyze the specimens, a specimen container buffer portion that holds a plurality of specimen containers holding the specimens, a conveyance device that delivers the specimen containers held in the specimen container buffer portion to the analysis units, and a control portion that, when the specimen containers are delivered to the plurality of analysis units, outputs synchronization signals to all of the plurality of analysis units at different timings regardless of whether there is an input of a delivery request from the analysis units during one operation cycle of the conveyance device. The analysis units deliver the specimen containers starting from the synchronization signals when a delivery request of the specimen containers is output.

Advantageous Effect

According to the invention, specimen containers can be conveyed to a plurality of analysis units without separately providing dedicated conveyance lines or affecting operation of the analysis units. Problems, configurations, and effects other than those described above will become apparent from the following description of embodiments.

BRIEF DESCRIPTION OF DRAWINGS

FIG. 1 is a diagram showing an automated analysis device according to an embodiment of the invention.

FIG. 2 is a diagram schematically showing a specimen rack and a specimen container used in the automated analysis device according to the embodiment of the invention.

FIG. 3 is a diagram showing a relationship of analysis cycles between a sampler portion and analysis units in the automated analysis device according to the embodiment of the invention.

FIG. 4 is a diagram schematically showing the sampler portion used in the automated analysis device according to the embodiment of the invention.

FIG. 5 is a diagram showing an example of time charts of control applied in an automated analysis device in the related art.

FIG. 6 is a diagram showing an example of time charts of control applied in the automated analysis device according to the embodiment of the invention.

FIG. 7 is a diagram showing an example of time charts of control applied in the automated analysis device according to the embodiment of the invention.

FIG. 8 is a diagram showing an automated analysis device according to another embodiment of the invention.

FIG. 9 is a diagram showing an example of time charts of control applied in the automated analysis device according to the other embodiment of the invention.

FIG. 10 is a diagram showing an example of time charts of control applied in the automated analysis device according to the other embodiment of the invention.

DESCRIPTION OF EMBODIMENTS

Automated analysis devices according to embodiments of the invention will be described with reference to FIGS. 1 to 9.

First, an automated analysis device will be schematically described with reference to FIGS. 1 to 4. FIG. 1 is a block diagram of the automated analysis device according to the invention. FIG. 2 is a diagram showing a specimen rack and a specimen container. FIG. 3 is a diagram showing a relationship of analysis cycles between a sampler portion and analysis units. FIG. 4 is a diagram schematically showing a sampler portion.

As shown in FIG. 1, an automated analysis device 100 that analyzes specimens includes a sampler portion 1 that places and collects a specimen rack 5, an analysis unit 2 to one side of the sampler portion 1, and an analysis unit 3 to the other side of the sampler portion 1.

The automated analysis device 100 according to the present embodiment is assumed to be an automated analysis device including a conveyance device that conveys the specimen rack 5 on which five specimen containers 7 are mounted as shown in FIG. 2.

The sampler portion 1 is a unit that places the specimen rack 5 into the automated analysis device 100, and delivers and conveys the specimen rack 5 held in a buffer portion 10 to the analysis units 2 and 3. According to the invention, the sampler portion 1 is operated at a cycle 90 as shown in FIG. 3. Among a plurality of analysis units 2 and 3 separately connected to the sampler portion 1, the cycle 90 is the same as a cycle 92 of the analysis unit 2 having a short analysis cycle instead of a cycle 93 of the analysis unit 3 having a long analysis cycle.

Next, the sampler portion 1 will be described in detail with reference to FIG. 4.

As shown in FIG. 4, the sampler portion 1 includes the buffer portion 10, a storage portion 11, an intake portion 12, an emergency rack intake 13, a conveyance portion 14, a specimen barcode reader 15, an emergency rack detection sensor 16, a specimen determination sensor 17, and a control portion 50.

In the sampler portion 1, the specimen rack 5 provided in the intake portion 12 is conveyed to the buffer portion 10 by the conveyance portion 14. The specimen determination sensor 17 is provided in an intermediate portion of the conveyance portion 14 to recognize the specimen containers 7 on the specimen rack 5. If it is determined that the specimen containers 7 are present, the specimen barcode reader 15 reads specimen barcodes attached to the specimen containers 7 and recognizes identification information of specimens. A patient is specified according to the identification information in an actual system.

The emergency rack intake 13 is a portion for providing one specimen rack 5 that holds the specimen containers 7 containing specimens which require an urgent measurement. In a case where an urgent measurement needs to be performed, when the specimen rack 5 is provided in the emergency rack intake 13, the emergency rack detection sensor 16 reads a specimen rack barcode 6 in which emergency information is recorded so as to recognize the specimen rack 5, the specimen rack 5 overtakes the specimen racks 5 provided in the intake portion 12 and is conveyed to the analysis units 2 and 3 via the buffer portion 10.

The buffer portion 10 has a rotor structure having a circular trajectory and has slots that hold, radically on a concentric circle, a plurality of specimen racks 5 on which a plurality of specimen containers 7 are placed on an outer circumference. Anyone of the specimen racks 5 is conveyed into or out from a requested destination by rotating the slots by the motor. With such a structure, it is not always necessary to sequentially process the specimen racks 5 that are placed first. That is, if one specimen rack 5 has a high priority, the specimen rack 5 would be processed first.

The conveyance portion 14 is connected to one point on the radial circumference of the buffer portion 10, and conveys the specimen racks 5 into or out of the radial circumference. When the point is at a position of 0 degree on the circumference, the circumference is connected with a draw-in line 21 to the analysis unit 2 at a position of +90 degrees on the circumference from the position where the conveyance portion 14 is connected and a draw-in line 31 to the analysis unit 3 at a position of −90 degrees on the circumference from the position where the conveyance portion 14 is connected, and the specimen racks 5 are conveyed into or out of the analysis units 2 and 3 (delivery process). The draw-in line 21 and the draw-in line 31 will be described later.

The specimen racks 5 that have completed dispensing in the analysis units 2 and 3 separately can wait in the buffer portion 10, wait for an output of a measurement result, and perform a process such as an automated re-inspection as needed. When the process is completed, the specimen racks 5 are conveyed to the storage portion 11 via the conveyance portion 14.

A control computer 4 is connected to the analysis units 2 and 3 and the sampler portion 1 via network lines 40. Each unit is operated via a user interface such as a display device 4a and an input device 4b.

Generally, the specimen racks 5 on which the specimen containers 7 are placed are provided in the intake portion 12. When an analysis is started, the specimen racks 5 are drawn into the buffer portion 10. According to a requested item, the specimen racks 5 are conveyed to the analysis unit 2 via the draw-in line 21 or conveyed to the analysis unit 3 via the draw-in line 31.

Thereafter, specimens are suctioned by an analysis unit specimen dispensing probe 22 or an analysis unit specimen dispensing probe 32. Thereafter, the specimens react with a reagent in a reaction vessel. A detector measures a characteristic of the reaction liquid to perform qualitative and quantitative analyses on the specimens. The specimen racks 5 in which the specimens have been suctioned are returned to the buffer portion 10 by being conveyed through the draw-in lines 21 and 31 in a reverse direction, and are finally collected to the storage portion 11.

The control computer 4 performs control relating to the analyses. In the invention, the control portion 50 provided in the sampler portion 1 performs a detailed part of the delivery process in which the specimen racks 5 are conveyed into or out the plurality of analysis units 2 and 3. Detailed control content will be described later.

Returning to FIG. 1, the analysis unit 2 is for a biochemical examination and the analysis unit 3 is for an immune examination, whose examination purposes and process capacities (analysis cycles: analysis process capacities per unit time) are different. In the present embodiment, for example, the analysis unit 2 is set to 450 tests/1 hour (8.0 seconds/1 cycle) and the analysis unit 3 is set to 120 tests/1 hour (30.0 seconds/1 cycle).

In this manner, the analysis units 2 and 3 do not have the same analysis cycles 92 and 93 of specimens, and the analysis cycles 92 and 93 of other analysis units 2 and 3 are not common multiples of the analysis units 2 and 3 having shortest analysis cycles 92 and 93. When the number of analyses scheduled to be performed up to a period that is a common multiple of the analysis cycles 92 and 93 of the plurality of analysis units 2 and 3 is 3% or more of the number of analyses per unit time required by the analysis units 2 and 3, it is determined to be of a high level. It should be noted that the specific number as described above is not always necessary, and it is needless to say that the number can be set according to the capacities required by the device.

The analysis unit 2 for a biochemical examination and the analysis unit 3 for an immune examination may have known configurations.

Although a case of different examination purposes and process capacities of the plurality of analysis units 2 and 3 that analyze the specimens is described, the analysis units may be of the same type. In addition, examination items and process capacities may be the same. In the case in which the purposes (examination items) and the process capacities are different, even if the purposes and the process capacities are the same, a process capacity of each analysis unit is maintained to a maximum degree.

Hereinafter, control in the control portion 50 will be described with reference to FIGS. 5 to 7. FIG. 5 is a diagram showing an example of time charts of control in an automated analysis device in the related art. FIGS. 6 and 7 are diagrams showing examples of time charts of control in the automated analysis device according to the present embodiment.

As described above, the analysis unit 2 is used for a biochemical analysis and the analysis unit 3 is used for an immune analysis. It is assumed that the analysis units measure different examination items. When the analysis units 2 and 3 are connected, generally the analysis units 2 and 3 do not have the same process capacity, but one of the analysis units 2 and 3 has a high process capacity and the other one has a low process capacity.

When the analysis units 2 and 3 having different process capacities are connected in this manner, the analysis unit 3 having a low process capacity affects a process capacity of a system. A ratio varies depending on the number of requests for one specimen. The number of items requested for the specimen varies depending on the specimen and there is no uniform definition.

When the analysis units 2 and 3 are connected, the analysis units 2 and 3 are connected via the buffer portion 10. Accordingly, a delivery process between the specimen rack 5 and one of the analysis units 2 and 3 cannot be performed when a delivery process between the specimen rack 5 and the other one of the analysis units 2 and 3 is performed.

As a result, as shown in FIG. 5, even when the analysis unit 3 normally performs an analysis process, the specimen rack 5 is not delivered to the analysis unit 3 due to the analysis unit 2. Accordingly, the analysis unit 3 may have an empty cycle and the process capacity may be lowered.

As shown in FIGS. 6 and 7, the control portion 50 provided in the sampler portion 1 outputs, to all of the plurality of analysis units 2 and 3, synchronization signals 90$s$1, 90$s$2, 90$s$3, 90$s$4, 90$s$5, and 90$s$6 whose output timings are spaced by one of the number of the connected analysis units 2 and 3 in one operation cycle when delivery processes 90$t$1, 90$t$4, 90$t$5, and 90$t$6 of the specimen racks 5 to the plurality of analysis units 2 and 3 are performed.

More specifically, in a case in which the delivery processes do not interfere with each other in one operation cycle, that is, a delivery request is not repeatedly input in the same analysis cycle, as shown in FIG. 6, the control portion 50 first outputs the synchronization signal 90$s$1 to the analysis unit 2 when the delivery process is performed to the analysis unit 2. The analysis unit 2 receives an input of the synchronization signal 90$s$1 and performs the delivery process 90$t$1 of the specimen racks 5 between the buffer portion 10 of the sampler portion 1 and the analysis unit 2.

Next, as shown in FIG. 6, the control portion 50 outputs the synchronization signal 90$s$2 to the analysis unit 3 immediately after the delivery process 90$t$1 of the specimen racks 5. However, since there is no delivery request for specimen racks, the analysis unit 3 ignores the synchronization signal 90$s$2.

Similarly, when the delivery process is performed only to the analysis unit 3, as shown in FIG. 6, the control portion 50 first outputs the synchronization signal 90$s$3 to the analysis unit 2. However, since there is no delivery request for specimen racks, the analysis unit 2 ignores the synchronization signal 90*s*3.

Next, as shown in FIG. 6, the control portion 50 outputs the synchronization signal 90*s*4 to the analysis unit 3 immediately after a period assumed to be required for the delivery process of the specimen racks 5 to the analysis unit 2. The analysis unit 3 receives an input of the synchronization signal 90*s*4 and performs the delivery process 90*t*4 of the specimen racks 5 between the buffer portion 10 of the sampler portion 1 and the analysis unit 3.

When the delivery processes interfere with each other in one operation cycle, that is, when the control portion 50 repeatedly input a delivery request in the same analysis cycle, the control portion 50 first outputs the synchronization signal 90*s*5 to the analysis unit 2 as shown in FIG. 7. The analysis unit 2 receives an input of the synchronization signal 90*s*5 and performs the delivery process 90*t*5 of the specimen racks 5 between the buffer portion 10 of the sampler portion 1 and the analysis unit 2.

As shown in FIG. 7, the control portion 50 outputs the synchronization signal 90*s*6 to the analysis unit 3 immediately after the delivery process 90*t*5 of the specimen racks 5. The analysis unit 3 receives an input of the synchronization signal 90*s*6 and performs the delivery process 90*t*6 of the specimen racks 5 between the buffer portion 10 of the sampler portion 1 and the analysis unit 3.

As shown in FIG. 7, when an assumed delivery request of the specimen racks 5 from the analysis unit 3 whose analysis cycle is not the same as the analysis cycle of the sampler portion 1 overlaps a break in the analysis cycle, the control portion 50 outputs a synchronization signal 90*s*7*a* in an analysis cycle that is one analysis cycle before the assumed delivery process and performs a delivery process 90*t*7*a*. When the delivery process cannot be performed in the analysis cycle that is one analysis cycle before the assumed delivery process, the control portion 50 outputs a synchronization signal 90*s*7*b* and performs a delivery process 90*t*7*b* in an analysis cycle that is one analysis cycle later than the assumed delivery process.

Although it is assumed in FIG. 1 that two analysis units are connected, other angles may be used as long as the two analysis units are connected at different phases. The number of analysis units to be connected is not limited to two. For example, three analysis units may be set at an interval of 90 degrees as shown in FIG. 8, which will be described later. The number of analysis units to be connected may be three or more.

Hereinafter, a case in which three analysis units 2, 3, and 9 are connected will be described with reference to FIGS. 8 to 10. FIG. 8 is a block diagram showing another automated analysis device according to the invention.

As shown in FIG. 8, an automated analysis device 100A includes a sampler portion 1A that places and collects the specimen racks 5 provided in the automated analysis device 100 shown in FIG. 1, the analysis unit 2 to a right side of the sampler portion 1A, the analysis unit 3 to a left side of the sampler portion 1A, and an analysis unit 9 to an opposite side of the sampler portion 1A and between the analysis unit 2 and the analysis unit 3.

Similar to the analysis units 2 and 3, the analysis unit 9 is also an analysis unit for a biochemical examination or an immune analysis. A process capacity of the analysis unit 9 is, for example, 90 tests/1 hour (40.0 seconds/1 cycle). The analysis unit 9 includes a draw-in line 91 and is used in a delivery process of the specimen racks 5 between a buffer portion 10A and the analysis unit 9.

The automated analysis device 100A is the same as the automated analysis device 100 shown in FIG. 1 in that a plurality of analysis units 2, 3, and 9 do not have the same analysis cycles 92, 93, and 99 of specimens (see FIG. 9) for all analysis units 2, 3, and 9, the sampler portion 1A is operated in the same cycle as the analysis unit 2 having a shortest analysis cycle, and the like.

The control computer 4 performs all processes including analyses in the automated analysis device 100A shown in FIG. 8, and a control portion 50A performs a detailed part of a delivery process in which the specimen racks 5 are conveyed into or out the plurality of analysis units 2, 3, and 9.

Next, the delivery process of the specimen racks 5 in the control portion 50A will be described with reference to FIGS. 9 and 10. FIGS. 9 and 10 are diagrams showing examples of time charts of control by the control portion 50A.

In a case in which three analysis units 2, 3, and 9 as shown in FIG. 8 are connected, the control portion 50A outputs, to all of the plurality of analysis units 2, 3, and 9, synchronization signals 90*s*8, 90*s*9, 90*s*10, 90*s*11, 90*s*12, 90*s*13, 90*s*14, 90*s*15, 90*s*16, 90*s*17, 90*s*18, and 90*s*19 whose output timings are spaced when the control portion 50A performs delivery processes 90*t*8, 90*t*12, 90*t*16, 90*t*17, and 90*t*19 of the specimen racks 5 to the plurality of analysis units 2, 3, and 9.

More specifically, when the control portion 50A performs the delivery process to the analysis unit 2 only, the control portion 50A first outputs the synchronization signal 90*s*8 to the analysis unit 2 as shown in FIG. 9. The analysis unit 2 receives an input of the synchronization signal 90*s*8 and performs the delivery process 90*t*8 of the specimen racks 5 between the buffer portion 10A of the sampler portion 1A and the analysis unit 2.

Next, the control portion 50A outputs the synchronization signal 90*s*9 to the analysis unit 3 immediately after the delivery process 90*t*8 of the specimen rack 5 as shown in FIG. 9. However, since there is no delivery request for specimen racks, the analysis unit 3 ignores the synchronization signal 90*s*9.

The control portion 50A outputs the synchronization signal 90*s*10 to the analysis unit 9 immediately after a period assumed to be required for the delivery process of the specimen racks 5 to the analysis unit 3. However, since there is no delivery request for the specimen racks, the analysis unit 9 ignores the synchronization signal 90*s*10.

Similarly, when the delivery process is performed to the analysis unit 3 only, the control portion 50A first outputs the synchronization signal 90*s*11 to the analysis unit 2 as shown in FIG. 9. However, since there is no delivery request for the specimen racks, the analysis unit 2 ignores the synchronization signal 90*s*11.

Next, the control portion 50A outputs the synchronization signal 90*s*12 to the analysis unit 3 immediately after a period assumed to be required for the delivery process of the specimen racks 5 to the analysis unit 2 as shown in FIG. 9. The analysis unit 3 receives an input of the synchronization signal 90*s*12 and performs the delivery process 90*t*12 of the specimen racks 5 between the buffer portion 10A of the sampler portion 1A and the analysis unit 3.

The control portion 50A outputs the synchronization signal 90*s*13 to the analysis unit 9 at a timing when the delivery process 90*t*12 is completed. However, since there is no delivery request for the specimen racks, the analysis unit 9 ignores the synchronization signal 90*s*13.

Similarly, when the delivery process is performed to the analysis unit 9 only, the control portion 50A first outputs the synchronization signal 90s14 to the analysis unit 2 as shown in FIG. 9. However, since there is no delivery request for the specimen racks, the analysis unit 2 ignores the synchronization signal 90s14.

Next, the control portion 50A outputs the synchronization signal 90s15 to the analysis unit 3 immediately after a period assumed to be required for the delivery process of the specimen racks 5 to the analysis unit 2 as shown in FIG. 9. However, since there is no delivery request for the specimen racks, the analysis unit 3 ignores the synchronization signal 90s15.

Then, the control portion 50A outputs the synchronization signal 90s16 to the analysis unit 9 immediately after a period assumed to be required for the delivery process of the specimen racks 5 to the analysis unit 3. The analysis unit 9 receives an input of the synchronization signal 90s16 and performs the delivery process 90t16 of the specimen racks 5 between the buffer portion 10A of the sampler portion 1A and the analysis unit 9.

When the delivery processes interfere with each other in one operation cycle, that is, when the control portion 50A repeatedly inputs a delivery request in the same analysis cycle from the analysis units 2 and 9, the control portion 50A first outputs the synchronization signal 90s17 to the analysis unit 2 as shown in FIG. 10. The analysis unit 2 receives an input of the synchronization signal 90s17 and performs the delivery process 90t17 of the specimen racks 5 between the buffer portion 10A of the sampler portion 1A and the analysis unit 2.

Next, the control portion 50A outputs the synchronization signal 90s18 to the analysis unit 3 immediately after the delivery process 90t17 of the specimen racks 5 as shown in FIG. 10. However, since there is no delivery request for the specimen racks, the analysis unit 3 ignores the synchronization signal 90s18.

Then, as shown in FIG. 10, the control portion 50A outputs the synchronization signal 90s19 to the analysis unit 9 immediately after a period assumed to be required for the delivery process of the specimen racks 5 to the analysis unit 3. The analysis unit 9 receives an input of the synchronization signal 90s19 and performs the delivery process 90t19 of the specimen racks 5 between the buffer portion 10A of the sampler portion 1A and the analysis unit 9.

Next, effects of the present embodiment will be described.

The automated analysis devices 100 and 100A according to the embodiments described above include a plurality of analysis units 2, 3, and 9 that analyze specimens, the buffer portion 10 and 10A that hold a plurality of specimen racks 5 on which the specimen containers 7 holding specimens are placed, the sampler portion 1 and 1A that convey the specimen racks 5 held in the buffer portion 10 and 10A to the analysis units 2, 3, and 9, and the control portion 50 and 50A that output synchronization signals, at different timings, to all of the plurality of analysis units 2, 3, and 9 when the specimen racks 5 are delivered to the plurality of analysis units 2, 3, and 9. The analysis units 2, 3, and 9 perform delivery processes of the specimen racks 5 starting from the synchronization signals.

This controls delivery operation of the specimen racks 5 to be performed by operation following synchronization signals issued by the sampler portion 1 and 1A. That is, since a delivery process of the specimen racks 5 is performed, starting from a synchronization signal, in synchronization with one analysis unit to which the synchronization signal is output among the plurality of connected analysis units, a conflict on a time axis can be prevented among the analysis units as if dedicated buffers are provided. Therefore, even when deliver processes of the plurality of specimen racks 5 are performed in the operation cycle 90 of the sampler portion 1 and 1A, control can be performed without stopping operation of an analysis unit. Therefore, a device in which, even when one analysis unit is busy, a process to the other analysis unit is not affected can be provided and a process capacity of the entire system can be maintained to a maximum degree.

Such a process is particularly suitable for medium and small automated analysis devices in which a plurality of (2 or 3) analysis units having different process capacities are connected to one buffer portion.

Since the sampler portion 1 and 1A are operated in the same cycle 90 as the analysis unit 2 having the shortest analysis cycle 92 among the plurality of analysis units 2, 3, and 9 that are connected to one another, a synchronization signal can be controlled to be output with reference to the analysis unit 2 that is assumed to have a highest delivery request of the specimen racks 5 so as to perform a delivery process, and the process capacity of the entire system can be more easily maintained to a maximum degree.

In one operation cycle, the control portion 50 and 50A can more reliably perform the delivery process of the specimen racks 5 without stopping operation of an analysis unit by spacing output timings of the synchronization signals output to the plurality of analysis units 2, 3, and 9 by one of the number of the connected analysis units 2, 3, and 9.

In one operation cycle, the control portion 50 and 50A first output a synchronization signal to the analysis unit 2 having the shortest analysis cycle 92, and sequentially output synchronization signals to the other analysis unit 3 and 9 other than the analysis unit 2 having the shortest analysis cycle 92 immediately after a period required for the delivery process of the specimen racks 5, so that the specimen racks 5 can be first delivered to the analysis unit 2 with no spare time and the delivery process of the specimen racks 5 can be performed stably.

In a case in which the synchronization signals are received when there is no request for the delivery process of the specimen racks 5, the plurality of analysis units 2, 3, and 9 ignore the synchronization signals, so that a load of the system can be reduced without operation corresponding to an unnecessary synchronization signal.

The plurality of analysis units 2, 3, and 9 do not have the same analysis cycles 92, 93, and 99 of specimens, or the analysis cycles 92, 93, and 99 of specimens are not the same for all of the analysis units 2, 3, and 9, and the analysis cycles 92, 93, and 99 of other analysis units 2, 3, and 9 are common multiples of the analysis units 2, 3, and 9 having shortest analysis cycles 92, 93, and 99. Alternatively, the analysis cycles 92, 93, and 99 of specimens are not all the same for all analysis units 2, 3, and 9, and the number of analyses scheduled to be performed up to a period that is a common multiple of the analysis cycles 92, 93, and 99 of the plurality of the analysis units 2, 3, and 9 is 3% or more the number of analyses per unit time required by the analysis units 2, 3, and 9. Even in such an automated analysis device, the delivery process of the specimen racks 5 or an analysis process can be performed without stopping operation of an analysis unit.

The buffer portion 10 and 10A have a rotor structure and the specimen racks 5 are held radically on a concentric circle, so that any one of the specimen racks 5 can be delivered in random order to the plurality of the analysis units 2, 3, and 9 without using a complicated structure.

The plurality of analysis units 2, 3, and 9 are arranged to the sampler portion 1 and 1A at an interval of 90 degrees so that the plurality of analysis units 2, 3, and 9 can be arranged without interference.

Other Aspects

The invention is not limited to the embodiments described above, and may include various modifications and applications. The embodiments described above have been described in detail for easy understanding of the invention, and are not necessarily limited to those including all the configurations described above.

For example, the embodiments described above describe a case in which the specimen racks 5 holding a plurality of specimen containers 7 are delivered as shown in FIG. 2. Alternatively, the invention may be applied to an automated analysis device including a conveyance device that delivers a specimen holder holding one specimen container 7.

Although the control portion 50 and 50A are provided in the sampler portion 1 and 1A, the control portion 50 and 50A may be mounted in the control computer 4.

REFERENCE SIGN LIST

1, 1A: sampler portion (conveyance device)
2, 3, 9: analysis unit
4: control computer
4a: display device
4b: input device
5: specimen rack
6: specimen rack barcode
7: specimen container
8: specimen barcode
10, 10A: buffer portion (specimen container buffer portion)
11: storage portion
12: intake portion
13: emergency rack intake
14: conveyance portion
15: specimen barcode reader
16: emergency rack detection sensor
17: specimen determination sensor
21, 31, 91: draw-in line
22, 32: analysis unit specimen dispensing probe
40: network line
50, 50A: control portion
90: operation cycle of sampler portion 1
92: operation cycle of analysis unit 2
93: operation cycle of analysis unit 3
99: operation cycle of analysis unit 9
90t1, 90t4, 90t5, 90t6, 90t7a, 90t7b, 90t8, 90t12, 90t16, 90t17,
90t19: delivery process
90s1, 90s4, 90s5, 90s6, 90s7a, 90s7b, 90s8, 90s12, 90s16, 90s17, 90s19: synchronization signal (valid)
90s2, 90s3, 90s9, 90s10, 90s11, 90s13, 90s14, 90s15, 90s18: synchronization signal (invalid)
100, 100A: automated analysis device

The invention claimed is:

1. An automated analysis device that analyzes specimens, the automated analysis device comprising:
a plurality of analysis units that analyze the specimens;
a specimen container buffer portion that holds a plurality of specimen containers holding the specimens;
a conveyance device that delivers the specimen containers held in the specimen container buffer portion to the analysis units; and
a control portion configured to output synchronization signals to all of the plurality of analysis units at different timings independently of the control portion receiving a delivery request from the analysis units during one operation cycle of the conveyance device, wherein the control portion is configured to space the different timings of the synchronization signals output to the plurality of analysis units based on a number of the analysis units;
the specimen containers are delivered to the analysis units from the specimen container buffer portion in response to the analysis units receiving the synchronization signals only in a case in which the control portion received the delivery request prior to outputting the synchronization signals,
the conveyance device operates in a same cycle as a first analysis unit having a shortest analysis cycle among the plurality of analysis units connected to each other,
the control portion is configured to output the synchronization signals to all of the plurality of analysis units at the different timings in the same cycle in which the conveyance device operates,
the different timings of the synchronization signals are determined based on a length of a delivery process of each of the specimen containers, and the length of the delivery process is equal to the shortest analysis cycle divided by a total number of the analysis units in the automated analysis device, and
in a case where a respective delivery process for respective specimen containers to a respective analysis unit does not occur, the control portion is further configured to output a subsequent synchronization signal to a subsequent analysis unit immediately after a period assumed to be required for the respective delivery process.

2. The automated analysis device according to claim 1, wherein the control portion is configured to first output the synchronization signals to the first analysis unit having the shortest analysis cycle, and sequentially output the synchronization signals to another analysis unit other than the first analysis unit having the shortest analysis cycle.

3. The automated analysis device according to claim 1, wherein the conveyance device delivers the specimen containers to the plurality of analysis units only in a case in which the synchronization signals output by the control portion are received by the analysis units when there is a delivery request for the specimen containers.

4. The automated analysis device according to claim 2, wherein the conveyance device delivers the specimen containers to the plurality of analysis units only in a case in which the synchronization signals output by the control portion are received by the analysis units when there is a delivery request for the specimen containers.

5. The automated analysis device according to claim 1, wherein an analysis cycle of other analysis units besides the first analysis unit is not a common multiple of the shorter analysis cycle.

6. The automated analysis device according to claim 1, wherein a number of analyses scheduled to be performed during a period that is a common multiple of analysis cycles of the plurality of the analysis units is 3% or more of a number of analyses per unit time required by the plurality of the analysis units.

7. The automated analysis device according to claim 1, wherein the specimen container buffer portion has a rotor structure, and the specimen containers are held radially on a concentric circle.

8. The automated analysis device according to claim 7, wherein the plurality of analysis units are arranged to the conveyance device at an interval of 90 degrees.

9. The automated analysis device according to claim 1, wherein the control portion and the specimen container buffer portion are provided in the conveyance device.

10. The automated analysis device according to claim 1, wherein the analysis units include a unit that performs a biochemical analysis and a unit that performs an immune analysis.

* * * * *